United States Patent [19]

Yoshida et al.

[11] Patent Number: 5,767,123
[45] Date of Patent: Jun. 16, 1998

[54] TOTAL PARENTERAL NUTRITION SOLUTION CONTAINING WATER-SOLUBLE VITAMIN B

[75] Inventors: Masanori Yoshida, Toyono-gun; Saburo Matsuda, Kyoto; Chie Tomioka, Yawata, all of Japan

[73] Assignee: Tanabe Seiyaku Co., Ltd., Osaka, Japan

[21] Appl. No.: 559,100

[22] Filed: Nov. 16, 1995

[30] Foreign Application Priority Data

Nov. 17, 1994 [JP] Japan .................... 6-282343

[51] Int. Cl.$^6$ .................................... A01N 43/78
[52] U.S. Cl. ................. 514/276; 604/56; 604/410
[58] Field of Search ................ 426/72; 514/276, 514/904; 544/327; 604/56, 410

[56] References Cited

U.S. PATENT DOCUMENTS

| | | | |
|---|---|---|---|
| 2,748,054 | 5/1956 | Jurist | 514/52 |
| 5,006,559 | 4/1991 | Askanazi et al. | 514/561 |
| 5,215,750 | 6/1993 | Keane, II | 424/440 |

FOREIGN PATENT DOCUMENTS

| | | |
|---|---|---|
| 0399341 | 11/1990 | European Pat. Off. . |
| 2629845 | 1/1978 | Germany . |
| 3505572 | 9/1985 | Germany . |
| 3519687 | 12/1986 | Germany . |
| 250466 | 10/1987 | Germany . |
| 575255 | 3/1982 | Japan . |
| 6174637 | 4/1986 | Japan . |
| 61-103823 | 5/1986 | Japan . |
| 1186822 | 7/1989 | Japan . |
| 804750 | 11/1958 | United Kingdom . |
| 820474 | 9/1959 | United Kingdom . |
| 955683 | 4/1964 | United Kingdom . |
| 2120939 | 12/1983 | United Kingdom . |
| 93/13767 | 7/1993 | WIPO . |
| 8503002 | 7/1995 | WIPO . |

OTHER PUBLICATIONS

Chemical Abstracts, vol. 112, No. 2, 8 Jan. 1990, p. 284, col. 2, No. 11941q.
Chemical Abstracts, vol. 99, No. 18, 31 Oct. 1983, p. 384, col. 1, No. 146124j.
Bowman, B.B. et al, JPEN, 1983, 7(6), pp. 567–568.
Scheiner, J.M. et al, Am. J. Hosp. Pharm. 1981, 38(12), pp. 1911–1913.
Scheiner, J.M. et al, Am. J. Hosp. Pharm. 1981, 38(12), pp. 1911–1913, abstract only, Dec. 1981.
Bowman, B.B. et al, JPEN, 1983, 7(6), pp. 567–568, abstract only, Dec. 1983.
Sim, A.J., Cont. Iss. Clin. Biochem. 1986, 4, pp. 221–231, abstract only.
Smith, J.L. et al, JPEN, 1988, 12(4), pp. 394–402, abstract only, Aug. 1988.
Tripp, M.G. et al, Am. J. Hosp. Pharm. 1990, 47(11), pp. 2496–2503, abstract only.

Primary Examiner—C. Warren Ivy
Assistant Examiner—Garth M. Dahlen
Attorney, Agent, or Firm—Birch, Stewart, Kolasch & Birch, LLP

[57] ABSTRACT

A TPN solution to be prepared before using which comprises two separate infusions of an amino acid-infusion and a saccharide-infusion wherein both of said infusions contain no sulfite ion, either one of said infusions contains a water-soluble vitamin B, a pH of the infusion containing a water-soluble vitamin B is acidic and a pH of the TPN solution prepared by mixing both infusions is neutral. According to the TPN solution of the present invention, a water-soluble vitamin B can be stably preserved in a TPN solution for a long term though it has been recognized that the water-soluble vitamin B could not be contained in a TPN solution. The present invention enables to practically use a TPN solution previously containing a water-soluble vitamin B.

4 Claims, No Drawings

1

TOTAL PARENTERAL NUTRITION SOLUTION CONTAINING WATER-SOLUBLE VITAMIN B

BACKGROUND OF THE INVENTION

The present invention relates to a novel total parenteral nutrition (TPN) solution containing an amino acid, a saccharide and a water-soluble vitamin B, and more particularly to a TPN solution to be prepared before using which comprises two separate infusions of an amino acid-infusion and a saccharide-infusion, both of said infusions containing no sulfite ion, either one of said infusions containing a water-soluble vitamin B, and is stable for a long period.

For a patient who cannot orally ingest a nutrient, it is essential to supply all nutrients such as an amino acid, a saccharide and an electrolyte through a vein. This way is called the total parenteral nutrition therapy, (TPN therapy). As a TPN solution employed in the TPN therapy, there has been known (1) a TPN solution containing a saccharide, an amino acid, a fat and an electrolyte (Japanese Unexamined Patent Publications No. 186822/1989, WO08503002 and EP-A-0 399 341), (2) an emulsion for injection comprising an amino acid and a fat (Japanese Unexamined Patent Publication No. 74637/1986), (3) a TPN solution comprising two separate infusions, one of which contains glucose and an electrolyte and the other of which contains an amino acid (Japanese Unexamined Patent Publications No. 52455/1982 and No. 103823/1986) and the like.

In the TPN therapy, an infusion containing a high concentration of saccharide is usually administered to a patient. When a saccharide is degraded in glycolytic pathway to be utilized as a source of energy, vitamin $B_1$ is consumed as a coenzyme. Therefore, vitamin $B_1$ is deficient and deficiency of vitamin $B_1$ results in production of lactic acid in patients who are subjected to the TPN therapy for a long term. At worst, some of the patients have difficulty in breathing and the like due to the severe lactic acidosis. Accordingly, it has been known that the use of a water-soluble vitamin B, particularly vitamin $B_1$, with the infusion containing a high concentration of saccharide is essential in the TPN therapy. However, vitamin $B_1$ is rapidly degraded by a sulfite ion which is contained in an amino acid-infusion and the like as a stabilizer. Thus a practical TPN solution previously containing a water-soluble vitamin B has not been developed.

An object of the present invention is to provide a TPN solution containing an amino acid, a saccharide and a water-soluble vitamin B wherein each ingredient is stable, which is excellent in view of nutrients.

This and the other objects of the present invention will become apparent from the description hereinafter.

SUMMARY OF THE INVENTION

It has now been found by the present inventors that when a TPN solution is divided into two separate infusions of an amino acid-infusion and a saccharide-infusion, and both of said infusions contain no sulfite ion, either one of the infusions contains a water-soluble vitamin B, a pH of the infusion containing a water-soluble vitamin B is acidic, a pH of the other infusion is approximately neutral and a pH of a TPN solution prepared by mixing both infusions is neutral, the water-soluble vitamin B, the amino acid-infusion and the saccharide-infusion can be stably preserved for a long term.

In accordance with the present invention, there is provided a TPN solution to be prepared before using which comprises two separate infusions of an amino acid-infusion and a saccharide-infusion wherein both of said infusions contain no sulfite ion, either one of said infusions contains a water-soluble vitamin B, a pH of the infusion containing a water-soluble vitamin B is acidic and a pH of the TPN solution prepared by mixing both infusions is neutral.

According to the TPN solution of the present invention, a water-soluble vitamin B can be stably preserved in a TPN solution for a long term though it has been hitherto recognized that the water-soluble vitamin B could not be contained in a TPN solution. The present invention enables to practically use a TPN solution previously containing a water-soluble vitamin B.

The TPN solution of the present invention can avoid complicated works in administering a water-soluble vitamin B at the same time when carring out the TPN therapy. Thus the advantage of the present invention is that it is possible to administer both the TPN solution and the water-soluble vitamin B without being contaminated with microbes, particulate matter and the like.

DETAILED DESCRIPTION OF THE INVENTION

In the present invention, the term "neutral" means a pH at which a TPN solution can be administered to human body, concretely pH of about 4 to about 8, preferably pH 5 to 7. The term "approximately neutral" means pH 5 to 8. The term "acidic" means a pH at which a water-soluble vitamin B is stable in an infusion containing thereof, concretely pH of about 2 to about 4, preferably pH 2 to 4, more preferably pH 2 to 3.

In the present invention, the amino acid-infusion containing no sulfite ion may be an amino acid-infusion usually used in this field. Concrete examples thereof include infusions containing L-isoleucine, L-leucine, L-valine, L-methionine, L-phenylalanine, L-tyrosine, L-tryptophan, L-threonine, L-arginine, L-histidine, L-alanine, L-proline, L-serine, glycine, L-lysine, L-aspartic acid, L-glutamic acid, L-cysteine, L-cystine, L-hydroxyproline and the like. These amino acids contained in the amino acid-infusion may be in a free form or in a form of a salt. An example of the salt of an amino acid is a salt thereof with an organic acid such as malic acid, oleic acid, acetic acid, glutamic acid or hydrochloric acid.

The ratio of these amino acids is not particularly limited and is determined according to the known index in this field such as (i) Vuj-N formula based on the required amount of an essential amino acid determined by Rose in 1944, (ii) the index reported by the FAO special commitee in 1957, (iii) the index based on human milk or egg amino acid composition reported by the FAO/WHO joint commitee in 1965 or (iv) the Fischer ratio of the amino acid composition in plasma, and the like. Then, the amino acid-infusion contains amino acids in a modified ratio of a ratio of an essential amino acid to a nonessential amino acid (so-called E/N ratio) or a ratio of an essential amino acid to a total amino acid (so-called E/T ratio), or in a ratio which is determined in consideration of a ratio of the branched chain amino acid to an essential amino acid or a nonessential amino acid, and the like.

Concrete examples of the amino acid composition exemplified without any limitation, are, for instance, an amino acid composition for a patient who underwent an operation (Japanese Unexamined Patent Publication No. 33446/1980 and No. 36457/1980), an amino acid composition wherein the essential amino acid content is high (Japanese Unexamined Patent Publication No. 8312/1981), an amino acid composition wherein the branched chain amino acid content is 29 to 33 w/w % and the L-cysteine content which is essential for neonates is increased (Japanese Examined Patent Publication No. 19363/1989), an amino acid composition for a patient with hypohepatia and neonates wherein a ratio of L-tyrosine to L-phenylalanine by weight is 1:12 to 1:17 and the L-lysine content of the total amino acid is at least 9.5 w/w % (Japanese Examined Patent Publication No. 28403/1991), an amino acid composition consisting branched chain amino acids for restraining disintegration of myoprotein (Japanese Examined Patent Publication No. 14646/1992) and the like.

In the amino acid-infusion in the present invention, the amino acid composition is not limited to those described in the above-mentioned patent publications. Based on those amino acid compositions, there can be suitably employed an amino acid composition wherein the composition of several kinds of amino acids is modified (for example, a ratio of an essential amino acid or a nonessential amino acid is increased or decreased within the scope in which any nutritionally remarkable difference is not caused, or alternatively, without changing the ratio of an essential amino acid to a nonessential amino acid, the amount of the essential amino acid or the nonessential amino acid is increased or decreased), an amino acid composition wherein a ratio of several kinds of amino acids to a total amino acid or a concentration is modified without changing the amino acid composition pattern, and an amino acid composition wherein an amino acid is exchanged with another amino acid which is recognized to be nutritionally equivalent (for example, cysteine, cystine and methionine as a sulfur-containing amino acid, phenylalanine and tyrosine as an aromatic amino acid, and the like).

Especially, Japanese Examined Patent Publications No. 19363/1989 and No. 28403/1991 describe an amino acid-infusion having a nutritionally excellent composition, and for the amino acid-infusion in the present invention, there can be suitably used an amino acid-infusion having the amino acid composition pattern or the amino acid composition concretely described in these publications, or an amino acid-infusion having the amino acid composition pattern or the amino acid composition modified within the nutritionally equivalent scope.

The concentration of amino acids in the amino acid-infusion is not particularly limited, and preferably the concentration is determined so that the concentration of the total amino acid in the TPN solution to be administered will be about 2 to about 10 w/w %.

In the TPN solution of the present invention, the saccharide to be contained in the other infusion (the saccharide-infusion), is not particularly limited so long as it is metabolized and utilized as a calorie source in vivo. Concrete examples of the saccharide include a reducing sugar such as glucose, fructose or maltose, a sugar alcohol such as xylitol, sorbitol or glycerol, and the like. Among these, the reducing sugar such as glucose, fructose or maltose is preferable. These saccharides may be used alone or in an admixture thereof.

The concentration of a saccharide in the saccharide-infusion may be determined in consideration of various conditions such as administration purpose, age, nutritional status and kind of disease of a patient to be administered, and preferably the concentration of a saccharide is about 15 to about 60 w/w % in the saccharide-infusion to be administered.

In the TPN solution of the present invention, either the amino acid-infusion or the saccharide-infusion contains a water-soluble vitamin B.

Concrete examples of the water-soluble vitamin B include vitamin $B_1$ (thiamine), vitamin $B_2$ (riboflavin), vitamin $B_6$ family (pyridoxine, pyridoxal, pyridoxamine and the like), vitamin $B_{12}$ family (cyanocobalamin and the like), niacin (nicotinic acid and nicotinamide), pantothenic acid, biotin, choline, folic acid and the like. Among these, vitamin $B_1$ is particularly important and therefore vitamin $B_1$ must be contained in the TPN solution to be administered. The water-soluble vitamin B may be used alone or in an admixture thereof.

The above-mentioned water-soluble vitamin B may be used in a form of a salt thereof with an acid such as hydrochloric acid, phosphoric acid or nitric acid.

In the TPN solution of the present invention, either one or both of the amino acid-infusion and the saccharide-infusion may contain an electrolyte, if desired.

Concrete examples of an ion to be supplied as the electrolyte include sodium ion, potassium ion, magnesium ion, calcium ion, chlorine ion, phosphate ion, zinc ion and the like which are essential for the living organism.

With respect to the ion source as the electrolyte, concrete examples of a sodium ion source include sodium hydroxide, sodium chloride, a sodium salt of an organic acid such as lactic acid, acetic acid, tartaric acid, succinic acid, citric acid or malic acid, a sodium salt of an amino acid such as glutamic acid or aspartic acid, and the like. Concrete examples of a potassium ion source include potassium hydroxide, potassium chloride, a potassium salt of an organic acid such as acetic acid, citric acid, tartaric acid, malic acid, gluconic acid or phthalic acid, a potassium salt of an amino acid such as aspartic acid, and the like. Concrete examples of a magnesium ion source include magnesium chloride, magnesium sulfate, a magnesium salt of an organic acid such as acetic acid, succinic acid or lactic acid, a magnesium salt of an amino acid such as aspartic acid, and the like. Concrete examples of a calcium ion source include calcium chloride, calcium gluconate and the like. Concrete examples of a chlorine ion source include hydrochloric acid, sodium chloride, potassium chloride, magnesium chloride, calcium chloride, a hydrochloride of an amino acid such as aspartic acid, and the like. Concrete examples of a zinc ion source include zinc chloride, zinc sulfate, a zinc salt of an organic acid such as acetic acid or lactic acid, and the like. Concrete examples of a phosphate ion source include phosphoric acid and the like. Concrete examples of phosphate ion and sodium ion or potassium ion source include disodium hydrogenphosphate, sodium dihydrogenphosphate, dipotassium hydrogenphosphate, potassium dihydrogenphosphate and the like.

In the present invention, it is preferable to add all electrolytes to an infusion containing a water-soluble vitamin B of which pH is acidic or to add a phosphate ion source and a calcium ion source to different infusions, respectively, because crystals of calcium phosphate might precipitate in an infusion of which pH is approximately neutral.

The above-mentioned electrolytes may be added in such amount as is not excess in consideration of required amount thereof in vivo. For example, it is suitable to add about 0 to about 100 mEq of sodium ion, about 0 to about 100 mEq of potassium ion, about 0 to about 40 mEq of magnesium ion, about 0 to about 40 mEq of calcium ion, about 0 to about 300 mEq of chlorine ion and about 0 to about 1000 mg of phosphorous (96.8 mEq as phosphate ion) per 1 l of the TPN solution of the present invention.

In the TPN solution of the present invention, a pH of the infusion containing a water-soluble vitamin B is acidic.

In the present invention, the TPN solution of which pH is neutral can be prepared by mixing a saccharide-infusion of which pH is adjusted to be acidic and an amino acid-infusion of which pH is adjusted to be approximately neutral or by mixing an amino acid-infusion of which pH is adjusted to be acidic and a saccharide-infusion of which pH is adjusted to be approximately neutral.

In the present invention, it is preferable to adjust a pH to be approximately neutral by addition of electrolytes which are needed by the TPN solution.

Therefore, in the preferable manner for adding the electrolytes, a phosphate ion source is added to an infusion containing a water-soluble vitamin B and the other electrolytes including a calcium ion source are added to the other infusion, or a calcium ion source is added to an infusion containing a water-soluble vitamin B and the other electrolytes including a phosphate ion source are added to the other infusion.

It is preferable to adjust a pH of a saccharide-infusion to be acidic and to adjust a pH of an amino acid-infusion to be approximately neutral, i.e., it is preferable that a water-soluble vitamin B is contained in the saccharide-infusion. It is particularly preferable that a water-soluble vitamin B and a phosphate ion source or a calcium ion source are contained in the saccharide-infusion and the saccharide-infusion is adjusted to be acidic, while the other electrolytes are contained in an amino acid-infusion and the amino acid-infusion is adjusted to be approximately neutral.

Concrete examples of the TPN solution include a TPN solution having a pH of 4 to 8 prepared by mixing an infusion containing a water-soluble vitamin B having a pH of 2 to 4 and the other infusion having a pH of 5 to 8, preferably a TPN solution having a pH of 5 to 7 prepared by mixing an infusion containing a water-soluble vitamin B having a pH of 2 to 3.5 and the other infusion having a pH of 5 to 8, more preferably a TPN solution having a pH of 5 to 7 prepared by mixing an infusion containing a water-soluble vitamin B having a pH of 2 to 3 and the other infusion having a pH of 6 to 7.5.

In the present invention, it is possible that vitamin $B_1$ is contained in one infusion being acidic and a water-soluble vitamin B except for vitamin $B_1$ is contained in the other infusion. Alternatively, if required, it is possible that vitamin $B_1$ is contained in one infusion and a vitamin except for a water-soluble vitamin B and a trace element are properly contained in either one or both of the infusions.

In the adjustment of pH of an infusion, there can be suitably used an organic acid such as succinic acid or malic acid, an inorganic acid such as hydrochloric acid, or phosphoric acid, an organic base such as tris(hydroxymethyl) aminomethane and an inorganic base such as sodium hydroxide, which are usually used for the adjustment of pH of an infusion.

Additionally, the TPN solution of the present invention can contain a fat in either one or both of an amino acid-infusion and a saccharide-infusion, if desired.

As the fat, a fat usually used in a fat emulsion can be suitably used in the TPN solution of the present invention, and concrete examples of the fat include a purified vagetable oil such as cotton seed oil, sesame oil, peanut oil, olive oil, safflower oil or soybean oil, a fish oil, a triglyceride of medium chain fatty acid having 8 to 12 carbon atoms such as Panasate, trade name, Nippon Oil & Fats Co., Ltd., Japan, and the like. These fats can be used alone or suitably in an admixture thereof.

To the infusion containing a fat, an additive such as an emulsifier or an emulsifying auxiliary may be added in a suitable amount so as to reduce the droplet size of the fat and stabilize it. Concrete examples of the emulsifier include a phospholipid, e.g. yolk phospholipid such as yolk lecithin, soybean phospholipid and the like. Concrete examples of the emulsifying auxiliary include a higher fatty acid having 12 to 32 carbon atoms such as oleic acid, lauric acid, myristic acid, palmitic acid, stearic acid or linoleic acid, a medium chain fatty acid having 8 to 12 carbon atoms such as caprylic acid or capric acid, a basic amino acid such as lysine, and the like. These emulsifiers and emulsifying auxiliaries can be used alone or in an admixture thereof.

With respect to a container used for the TPN solution of the present invention, in order to mix an amino acid-infusion and a saccharide-infusion before using, there can be used a container having a structure which makes it possible to prepare a TPN solution by mixing two separate infusions to be one infusion with no complicated works without microbial and particulate matter contamination when the TPN solution is administered to a patient, irrespective of a material and shape of the container.

One example of such container is, for instance, container having a structure wherein an amino acid-infusion and a saccharide-infusion are packed into separate containers, which are connected with each other at a connection part, and a separating means which is easily broken by external force is provided in the connection part of the containers. Concrete examples of the separating means include a cock easily turned on, a partition easily broken by pushing, or a pin easily cut by pushing or bending.

The container into which the TPN solution of the present invention is packed, is not particularly limited so long as it is a container which is obtained by forming a material such as glass, a soft plastic or a rigid plastic into a shape of e.g. a bag, a bottle or the like. Particularly a preferred container is a container in a form of a bag made of a soft plastic, a bottle made of a rigid plastic, and the like.

Concrete examples of the soft plastic include a film made of, for example, a vinyl polymer such as polyethylene, polypropylene, poly(vinyl chloride), poly(vinyl acetate), a polyolefin or polystyrene; a copolymer of ethylene and a vinyl monomer such as vinyl acetate, vinyl alcohol (as a vinyl monomer unit), vinyl acetoacetal, acrylic acid, ethyl acrylate, methacrylic acid or maleic anhydride; a polycarbonate; a polyester; a nylon; vinyl chloride-vinyl acetate copolymer; ethylene fluoride-vinylidene chloride copolymer; a vinylidene chloride-coated nylon; or the like. Alternatively, a soft plastic may be a composite film suitably laminated with double or multiple layers comprising the above-mentioned film and, for example, a vinyl polymer such as polyethylene, polypropylene, ethylene-propylene copolymer, poly(vinyl acetate), polybutadiene, polystyrene or poly(vinyl alcohol); a metallic foil made of, for example, aluminium or the like; a nylon; cellophane; or the like.

Among these films, there can be suitably used a film comprising ethylene-propylene copolymer, polyethylene, polypropylene, poly(vinyl chloride), crosslinked ethylene-vinyl acetate copolymer, ethylene-vinyl alcohol copolymer, polypropylene/poly(vinyl alcohol)/polyethylene, nylon/poly (vinyl alcohol)/polyethylene, a vinylidene chloride-coated nylon/polyethylene, and the like.

Concrete examples of the rigid plastic include polyethylene, polypropylene, polyamide, poly (tetrafluoroethylene), a polycarbonate, acetylcellulose, FR PET (Fiber Reinforce-Polyethylene terephthalate) and the like. Among these rigid plastics, polyethylene, polypropylene, a polycarbonate and the like are preferable.

A preferred embodiment of the present invention include, for example, that using an air-permeable bag made of a soft plastic which has two compartments connected with each other and separated by a separating means, an amino acid-infusion is packed into one compartment of the bag and a saccharide-infusion is packed into the other compartment and further the bag is put into an airtight container. The airtight container may be prepared from, for example, vinyl chloride-vinyl acetate copolymer; ethylene fluoride-vinylidene chloride copolymer; a copolymer of ethylene and a vinyl monomer such as vinyl alcohol, acrylic acid, ethyl acrylate, methacrylic acid or maleic anhydride; a vinylidene chloride-coated nylon; polyethylene; polypropylene.

As an air-permeable container, there can be suitably used a container made of, among the above-mentioned soft plastics, a soft plastic comprising a polymeric film having an air permeability of 50 to 1000 ml $(STP)/m^2$, 24 h at 20° C. and at a relative humidity (RH) of 65%. As an airtight container, there can be suitably used, for example, a container made of such a polymeric film as has an oxygen permeability of at most 5 ml $(STP)/m^2$, 24 h, preferably at most 1 ml $(STP)/m^2$, 24 h at 20° C. and at a relative humidity of 60% in case of expressing of airtight degree with the oxygen permeability.

In the above-mentioned embodiment of the present invention, the air in a space between the airtight container and the air-permeable container in a form of the above-mentioned double package may be replaced with nitrogen gas, and also an oxygen absorber may be put therein. This case is advantageous because the storage stability of the infusion can be increased.

Concrete examples of the oxygen absorber include (1) a matter wherein iron carbide, an iron carbonyl compound, an iron oxide, an iron powder, an iron hydroxide or ferrosilicon, is coated with a metal halide, (2) a mixture of a dithionite; and (a) an alkaline earth metal hydroxide or an alkali earth metal carbonate, (b) an activated carbon and water, (c) a compound having water of crystallization, (d) an alkaline substance or (e) an alcohol group, (3) a mixture of an alkaline earth metal sulfite; and (a) an iron (II) compound, (b) a salt of a transition metal, (c) a salt of aluminium, (d) an alkali compound containing an alkaline metal or an alkaline earth metal, (e) an alkali compound containing nitrogen or (f) an ammonium salt, (4) a mixture of iron or zinc; and sodium sulfate monohydrate; or a mixture of iron or zinc; sodium sulfate monohydrate; and a metal halide, (5) a mixture of iron, copper, tin, zinc or nickel; sodium sulfate heptahydrate or sodium sulfate decahydrate; and a metal halide, (6) a mixture of a transition metal of the fourth period in the periodic table; tin or antimony; and water, or a mixture of a transition metal of the forth period in the periodic table; tin or antimony; water; and a metal halide, (7) a mixture of an alkaline metal sulfite, ammonium sulfite, an alkaline metal hydrogensulfite, ammonium hydrogensulfite, an alkaline metal pyrosulfite, or ammonium pyrosulfite; a salt of a transition metal or a salt of aluminium; and water, and the like. Alternatively, the commercially available oxygen absorber can be also used, and the concrete examples of the commercially available oxygen absorber include AGELESS (registered trademark, Mitsubishi Gas Chemical Company, Inc., Japan), MODURAN (registered trademark, NIPPON KAYAKU CO., LTD., Japan), and the like.

As to the above-mentioned oxygen absorber, it is preferable that an oxygen absorber in a form of powder is put into an air-permeable small pouch in a suitable amount and used, or an oxygen absorber in a form of a tablet may be used as it is without being packaged.

The TPN solution of the present invention can be obtained by preparing an amino acid-infusion and a saccharide-infusion according to a usual process and filling the containers (compartments) mentioned before with the amino acid-infusion and the saccharide-infusion.

The process for preparing the TPN solution of the present invention is concretely explained below. For example, an amino acid and a saccharide are dissolved in distilled water for injection without or with warming them, respectively, in such an amount as is the desired amount to be contained in the resulting TPN solution to prepare an amino acid-infusion and a saccharide-infusion. Then, a water-soluble vitamin B is added to either one of the amino acid-infusion and the saccharide-infusion, and an electrolyte and the like are added to either one or both of the amino acid-infusion and the saccharide-infusion. The pH of the infusion containing the water-soluble vitamin B is adjusted to be acidic and the pH of the other infusion is adjusted to be approximately neutral with a suitable organic acid, inorganic acid, organic base or inorganic base or the like, respectively. Then, each of the obtained amino acid-infusion and the saccharide-infusion is filtered through a membrane filter such as Millipore filter (trade name, NIHON MILLIPORE LTD.), and is put into each compartment of a container having a structure which makes it possible to obtain one infusion by mixing separated two infusions. After deairating the air in the infusions and in the space of the container with nitrogen gas, the container is hermetically sealed and heat sterilization is carried out under nitrogen gas. After the sterilization, the container is put into a bag made of an air-impermeable film, together with an oxygen absorber and the bag is hermetically sealed to obtain the TPN solution of the present invention.

The present invention also includes a TPN solution which is obtained by mixing an amino acid-infusion and a saccharide-infusion.

The present invention is more specifically described and explained by the following Experimental Examples and Examples in which all per cents and parts are by weight unless otherwise noted. It is to be understood that the present invention is not limited to the Examples, and various changes and modifications can be made in the invention without departing from the spirit and scope thereof.

EXPERIMENTAL EXAMPLE 1

Method (1) Vitamin $B_1$ (1.5 mg) was dissolved in the amino acid-infusion (300 ml) prepared according to the ingredients and amounts described in Table 1 to prepare amino acid-infusions A to D containing vitamin $B_1$. In preparation of each infusion, sodium sulfite (150 mg) was added to each of the infusions C and D, the infusions A and C were adjusted to pH 3 and the infusions B and D were adjusted to pH 4, with hydrochloric acid. Each of the infusions A to D was filtered through a membrane filter having a pore size of 0.22 μm.

TABLE 1

| Ingredient | Amount (mg) |
|---|---|
| L-Isoleucine | 850 |
| L-Leucine | 1350 |
| L-Valine | 900 |
| L-Methionine | 390 |
| L-Phenylalanine | 770 |
| L-Tyrosine | 50 |
| L-Threonine | 480 |

TABLE 1-continued

| Ingredient | Amount (mg) |
|---|---|
| L-Alanine | 860 |
| L-Proline | 640 |
| L-Serine | 420 |
| Glycine | 550 |
| L-Aspartic acid | 50 |
| L-Glutamic acid | 50 |
| L-Arginine | 1110 |
| L-Histidine | 470 |
| Lysine malate | 1216 |
| (L-Lysine contained therein) | (800) |
| L-Tryptophan | 160 |
| Cysteine malate | 155 |
| (L-Cysteine contained therein) | (100) |
| Distilled water for injection | Suitable amount |
| Total amount | 100 ml |

(2) Each of thus obtained infusions A to D was filled in a volume of 25 ml into a bag made of high density polyethylene, and the bag was hermetically sealed and then subjected to a steam sterilization under high pressure at 105° C. for 10 minutes.

(3) Each vitamin $B_1$ content in the obtained infusions A to D was determined by a high performance liquid chromatography (wavelength: 260 nm, mobile phase: phosphate buffer). The percents of residual vitamin $B_1$ were calculated by comparison with vitamin $B_1$ content in the infusion before sterilization.

Results

The results are shown in Table 2.

TABLE 2

| | Infusion of the present invention | | Control infusion | |
|---|---|---|---|---|
| | A | B | C | D |
| Actual vitamin $B_1$ ratio (%) | 102.3 | 96.9 | 75.2 | 0 |

As shown in Table 2, in the amino acid-infusions C and D containing sodium sulfite, the vitamin $B_1$ content was decreased by the heat sterilization. Particularly in the infusion D of pH 4, the vitamin $B_1$ content was decreased after the sterilization to be below the detection limit. On the other hand, in the amino acid-infusions A and B containing no sulfite ion of the present invention, the vitamin $B_1$ content did not substantially vary even after the sterilization.

EXPERIMENTAL EXAMPLE 2

Method (1) The ingredients described in Table 3 were dissolved in distilled water for injection without or with warming to prepare infusions E to H. In preparation of each infusion, the infusion E was adjusted to pH 3 with succinic acid and the infusions F to H were adjusted to pH 3 with hydrochloric acid. Each of the infusions E to H was filtered through a membrane filter having a pore size of 0.22 μm.

TABLE 3

| | Saccharide-infusion | | Amino acid-infusion | |
|---|---|---|---|---|
| Ingredient | E | F | G | H |
| Glucose | 120.0 g | 120.0 g | — | — |
| Amino acid-infusion (prepared according to the ingredients and amounts described in Table 1) | — | — | 900 ml | 300 ml |
| Vitamin $B_1$ | 3.5 mg | 3.5 mg | 4.5 mg | 1.5 mg |
| Sodium L-lactate | — | 3.362 g | — | 3.362 g |
| Calcium gluconate | — | 1.906 g | — | 1.906 g |
| Sodium chloride | — | 1.169 g | — | 1.169 g |
| Potassium acetate | — | 1.168 g | — | 1.168 g |
| Potassium dihydrogenphosphate | — | 1.100 g | — | 1.100 g |
| Magnesium chloride | — | 1.017 g | — | 1.017 g |
| Potassium chloride | — | 0.746 g | — | 0.746 g |
| Zinc sulfate | — | 5.8 mg | — | 5.8 mg |
| Distilled water for injection | Suitable amount | Suitable amount | — | — |
| Total amount | 700 ml | 700 ml | 900 ml | 300 ml |

(2) Each of thus obtained infusions E to H was filled in a volume of 25 ml into a bag made of high density polyethylene. After each infusion and the space in the bag were deairated by nitrogen gas, each bag was hermetically sealed and subjected to steam sterilization under high pressure at 105° C. for 10 minutes.

(3) Each of thus obtained bags and an oxygen absorber were put in a bag made of an air-impermeable film and after replacing the air therein with nitrogen gas, each bag was hermetically sealed.

(4) After storage at 50° C. and at a relative humidity (RH) of 75% for 40 days, each vitamin $B_1$ content in the infusion was determined by a high performance liquid chromatography. The parcents of residual vitamin $B_1$ were calculated by comparison with vitamin $B_1$ content in the infusion stored in a cold place.

Also, the stability of each infusion was examined by measurement of the transmittance with wavelength of 400 nm and observation of appearance.

Results

The results are shown in Table 4.

TABLE 4

| | Saccharide-infusion | | Amino acid-infusion | |
|---|---|---|---|---|
| | E | F | G | H |
| Actual vitamin $B_1$ ratio (%) | 93.0 | 94.2 | 88.4 | 84.7 |
| Transmittance (%) | 99.88 | 95.82 | 96.75 | 96.36 |
| Observation of appearance | Each infusion was colorless and transparent | | | |

As shown in Table 4, it is shown that each of the infusions E to H containing no sulfite ion contains vitamin $B_1$ in a high concentration without decreasing even after stored at 50° C. and at a relative humidity (RH) of 75% for long period as long as 40 days and the quality thereof was good.

EXPERIMENTAL EXAMPLE 3

Method (1) Vitamin $B_1$ (5 mg), phosphoric acid (395 mg) and glucose (120 g) were mixed and dissolved into a suitable amount of a distilled water for injection, and to the resulting solution was added a distilled water for injection to make the total amount of 700 ml. The solution was adjusted to pH 2.5, 3.0, 3.5 or 4.0 to give saccharide-infusions X1 to X4.

(2) In an amino acid-infusion (300 ml) prepared according to the ingredients and amounts described in Table 1, there were dissolved sodium L-lactate (3.362 g), calcium gluconate (1.906 g), sodium chloride (1.169 g), potassium acetate (1.168 g), potassium hydroxide (0.459 g), magnesium chloride (1.017 g), potassium chloride (0.746 g) and zinc sulfate (5.8 mg), successively. The resulting solution was adjusted to pH 6.0, 6.5, 7.0 or 7.5 to give amino acid-infusions Y1 to Y4.

(3) Each of the saccharide-infusions X1–X4 (700 ml) and each of the amino acid-infusions Y1–Y4 (300 ml) were mixed in all combinations to prepare sixteen kinds of TPN solutions and each of pH values of the TPN solutions was measured.

Results

The results are shown in Table 5.

TABLE 5

|  | Saccharide-infusion | | | |
| --- | --- | --- | --- | --- |
|  | X1 (pH 2.5) | X2 (pH 3.0) | X3 (pH 3.5) | X4 (pH 4.0) |
| Amino acid-infusion | | | | |
| Y1 (pH 6.0) | 5.6 | 5.7 | 5.7 | 5.8 |
| Y2 (pH 6.5) | 5.9 | 6.1 | 6.1 | 6.1 |
| Y3 (pH 7.0) | 6.1 | 6.3 | 6.3 | 6.4 |
| Y4 (pH 7.5) | 6.4 | 6.6 | 6.6 | 6.7 |

As shown in Table 5, it was found that, when the saccharide-infusion having a pH of 2.5 to 4.0 containing phosphoric acid and vitamin $B_1$ and the amino acid-infusion having a pH of 6.0 to 7.5 containing electrolytes except for phosphoric acid were mixed, there was prepared the TPN solution having a pH of 5.6 to 6.7, which is suitable to be administered to a human body.

EXAMPLE 1

(1) The ingredients (a) in such amounts as described in Table 6 except for L-cysteine were dissolved in distilled water for injection (800 ml) with heating at 90° C., and after cooling the resulting solution, L-cysteine was dissolved therein. The obtained solution was adjusted to pH 7.0 with succinic acid and further a suitable amount of distilled water for injection was added thereto to make the total amount of 1000 ml. Thus an amino acid-infusion was prepared. The amino acid-infusion was filtered through Millipore filter GSWP04700 (trade name, NIHON MILLIPORE LTD.) having a pore size of 0.22 μm and filled into the first compartment of a bag having two compartments for infusion and then the first compartment was hermetically sealed. The bag was made of a soft plastic (crosslinked ethylene-vinyl acetate copolymer) and had a separating means which is easily broken by external force at the separating part thereof.

(2) The ingredients (b) in such amounts as described in Table 6 except for thiamine hydrochloride were dissolved in distilled water for injection (800 ml) with warming at 60° C. and after cooling the resulting solution, thiamine hydrochloride was dissolved therein. The obtained solution was adjusted to pH 3.5 with succinic acid and further a suitable amount of distilled water for injection was added thereto to make the total amount of 1000 ml. Thus a saccharide-infusion was prepared. The saccharide-infusion was filtered through Millipore filter having a pore size of 0.22 μm, and filled into the second compartment of the bag wherein the above-mentioned amino acid-infusion was filled into the first compartment, and then the second compartment was hermetically sealed.

(3) The bag containing both infusions was heat-sterilized at 105° C. for 10 minutes, and then the bag and an oxygen absorber (AGELESS, Mitsubishi Gas Chemical Company, Inc., Japan) were put in an oxygen-impermeable bag made of a film of poly(vinyl alcohol) resin. The bag was hermetically sealed and then the TPN solution of the present invention was obtained.

TABLE 6

| Ingredient | Amount |
| --- | --- |
| (a) L-Isoleucine | 3.4 g |
| L-Leucine | 7.5 g |
| L-Valine | 2.7 g |
| L-Methionine | 2.5 g |
| L-Phenylalanine | 6.0 g |
| L-Tyrosine | 0.3 g |
| L-Threonine | 3.5 g |
| L-Alanine | 4.0 g |
| L-Proline | 2.0 g |
| L-Serine | 1.0 g |
| Glycine | 6.5 g |
| L-Aspartic acid | 2.5 g |
| L-Glutamic acid | 4.5 g |
| L-Arginine | 4.6 g |
| L-Histidine | 5.2 g |
| Lysine malate | 8.0 g |
| L-Tryptophan | 1.0 g |
| L-Cysteine | 0.6 g |
| Potassium dihydrogenphosphate | 2.5 g |
| Potassium acetate | 4.0 g |
| Magnesium chloride | 1.5 g |
| Sodium chloride | 5.0 g |
| Zinc sulfate | 10 mg |
| (b) Glucose | 300 g |
| Calcium gluconate | 3.6 g |
| Thiamine hydrochloride | 5 mg |

EXAMPLE 2

(1) The ingredients (a) in such amounts as described in Table 7 except for L-cysteine and thiamine hydrochloride were dissolved in distilled water for injection (400 ml) with heating at 90° C., and after cooling the resulting solution, L-cysteine and thiamine hydrochloride were dissolved therein. The obtained solution was adjusted to pH 3.5 with malic acid and further a suitable amount of distilled water for injection was added thereto to make the total amount of 500 ml. Thus an amino acid-infusion was prepared. The amino acid-infusion was filtered through Millipore filter having a pore size of 0.22 μm and filled into the first compartment of a bag having two compartments for infusion and then the first compartment was hermetically sealed. The bag was made of a soft plastic (crosslinked ethylene-vinyl acetate copolymer).

(2) The ingredients (b) in such amounts as described in Table 7 were dissolved in distilled water for injection (400 ml) with warming at 60° C . After cooling the resulting solution, the resulting solution was adjusted to pH 6.0 with tris (hydroxymethyl)aminomethane and further a suitable amount of distilled water for injection was added thereto to make the total amount of 500 ml. Thus a saccharide-infusion was prepared. The saccharide-infusion was filtered through Millipore filter having a pore size of 0.22 μm, and filled into the second compartment of the bag wherein the above-mentioned amino acid-infusion was filled into the first compartment, and then the second compartment was hermetically sealed.

(3) The bag containing both infusions was heat-sterilized at 100° C. for 15 minutes, and then the bag and an oxygen absorber (AGELESS, Mitsubishi Gas Chemical Company, Inc., Japan) was put in an oxygen-imparmeable bag made of a film of poly(vinyl alcohol) resin. The bag was hermetically sealed and then a TPN solution of the present invention was obtained.

TABLE 7

| Ingredient | Amount |
| --- | --- |
| (a) L-Isoleucine | 3.4 g |
| L-Leucine | 5.4 g |
| L-Valine | 3.6 g |
| L-Methionine | 1.56 g |
| L-Phenylalanine | 3.08 g |
| L-Tyrosine | 0.2 g |
| L-Threonine | 1.92 g |
| L-Alanine | 3.44 g |
| L-Proline | 2.56 g |
| L-Serine | 1.68 g |
| Glycine | 2.2 g |
| L-Aspartic acid | 0.2 g |
| L-Glutamic acid | 0.2 g |
| L-Arginine | 4.44 g |
| L-Histidine | 1.88 g |
| Lysine malate | 3.45 g |
| L-Tryptophan | 6.4 g |
| L-Cysteine | 6.2 g |
| Calcium gluconate | 1.2 g |
| Thiamine hydrochloride | 5 mg |
| (b) Glucose | 170 g |
| Potassium acetate | 1.5 g |
| Magnesium chloride | 0.5 g |
| Potassium dihydrogenphosphate | 1.0 g |
| Sodium L-lactate | 2.5 g |
| Sodium chloride | 1.0 g |
| Potassium chloride | 0.5 g |

EXAMPLE 3

(1) The ingredients (a) in such amounts as described in Table 8 except for L-cysteine were dissolved in distilled water for injection (400 ml) with heating at 90° C., and after cooling the resulting solution, L-cysteine was dissolved therein. The obtained solution was adjusted to pH 7.0 with malic acid and further a suitable amount of distilled water for injection was added thereto to make the total amount of 500 ml. Thus an amino acid-infusion was prepared. The amino acid-infusion was filtered through Millipore filter having a pore size of 0.22 μm and filled into the first compartment of a bag having two compartments for infusion and then the first compartment was hermetically sealed. The bag was made of a soft plastic (crosslinked ethylene-vinyl acetate copolymer).

(2) The ingredients (b) in such amounts as described in Table 8 except for thiamine hydrochloride were dissolved in distilled water for injection (400 ml) with warming at 60° C. and after cooling the resulting solution, thiamine hydrochloride was dissolved therein. The obtained solution was adjusted to pH 3.5 with tris(hydroxymethyl)aminomethane and further a suitable amount of distilled water for injection was added thereto to make the total amount of 500 ml. Thus a saccharide-infusion was prepared. The saccharide-infusion was filtered through Millipore filter having a pore size of 0.22 μm, and filled into the second compartment of the bag wherein the above-mentioned amino acid-infusion was filled into the first compartment, and then the second compartment was hermetically sealed.

(3) The bag containing both infusions was heat-sterilized at 100° C. for 15 minutes, and then the bag and an oxygen absorber (AGELESS, Mitsubishi Gas Chemical Company, Inc., Japan) were put in an oxygen-imparmeable bag made of a film of poly(vinyl alcohol) resin. The bag was hermetically sealed and then the TPN solution of the present invention was obtained.

TABLE 8

| Ingredient | Amount |
| --- | --- |
| (a) L-Isoleucine | 3.4 g |
| L-Leucine | 5.4 g |
| L-Valine | 3.6 g |
| L-Methionine | 1.56 g |
| L-Phenylalanine | 3.08 g |
| L-Tyrosine | 0.2 g |
| L-Threonine | 1.92 g |
| L-Alanine | 344 g |
| L-Proline | 2.56 g |
| L-Serine | 1.68 g |
| Glycine | 2.2 g |
| L-Aspartic acid | 0.2 g |
| L-Glutamic acid | 0.2 g |
| L-Arginine | 4.44 g |
| L-Histidine | 1.88 g |
| Lysine malate | 3.45 g |
| L-Tryptophan | 6.4 g |
| L-Cysteine | 6.2 g |
| Potassium acetate | 1.5 g |
| Calcium gluconate | 1.2 g |
| Magnesium chloride | 0.5 g |
| Zinc sulfate | 10 mg |
| Potassium hydroxide | 0.31 g |
| Sodium L-lactate | 2.5 g |
| Sodium chloride | 1.0 g |
| Potassium chloride | 0.5 g |
| (b) Glucose | 170 g |
| Phosphoric acid | 0.4 g |
| Thiamine hydrochloride | 5 mg |

EXAMPLE 4

(1) The ingredients (a) in such amounts as described in Table 9 except for soybean oil, yolk lecithin, oleic acid and L-lysine, were dissolved in distilled water for injection (200 ml) with heating at 90° C. , and to the resulting solution, a suitable amount of distilled water for injection was added to make the total amount of 250 ml. Then the obtained solution was filtered through Millipore filter having a pore size of 0.22 μm to obtain an amino acid-solution.

(2) The ingredients, soybean oil, yolk lecithin, oleic acid and L-lysine, excluded above in such amounts as described in Table 9 were added to distilled water for injection (200 ml), and dispersed by means of a homomixer (URTRA-TURRAX, TOKUSHU KIKA KOGYO CO., LTD.). Then to the resulting dispersion, was added a suitable amount of distilled water for injection to make the total amount of 250 ml. The obtained crude emulsion was emulsified at 60° C. at 500 to 600 kgf/cm$^2$ in 10 cycles by means of a high pressure homogenizer (MANTON-GAULIN MODEL 15M, MANTON-GAULIN MANUFACTURING CO., INC. USA). The obtained fine emulsion was filtered through Millipore filter having a pore size of 0.22 μm to obtain a fat emulsion.

(3) The fat emulsion (250 ml) obtained in the above (2) was added to the amino acid-solution (250 ml) obtained in the above (1) to obtain an amino acid-infusion. The amino acid-infusion was adjusted to pH 8.0 with malic acid, and filled into the first compartment of a bag for infusion, and then the first compartment was hermetically sealed. The bag was made of a soft plastic (crosslinked ethylene-vinyl acetate copolymer).

(4) The ingredients (b) in such amounts as described in Table 9 except for thiamine hydrochloride were dissolved in distilled water for injection (400 ml) with warming at 60° C. and after cooling the resulting solution, thiamine hydrochloride was dissolved therein. The obtained solution was adjusted to pH 4.0 with malic acid and further a suitable amount of distilled water for injection was added thereto to make the total amount of 500 ml. Thus a saccharide-infusion was prepared. The saccharide-infusion was filtered through Millipore filter having a pore size of 0.22 μm, and filled into the second compartment of the bag wherein the above-mentioned amino acid-infusion was filled into the first compartment, and then the second compartment was hermetically sealed.

(5) The bag containing both infusions was heat-sterilized at 100° C. for 15 minutes, and then the bag and an oxygen absorber (AGELESS, Mitsubishi Gas Chemical Company, Inc., Japan) were put in an oxygen-impermeable bag made of a film of poly(vinyl alcohol) resin. The bag was hermetically sealed and then the TPN solution of the present invention was obtained.

TABLE 9

| Ingredient | Amount |
| --- | --- |
| (a) L-Isoleucine | 1.7 g |
| L-Leucine | 3.8 g |
| L-Valine | 1.4 g |
| L-Methionine | 1.0 g |
| L-Phenylalanine | 2.8 g |
| L-Tyrosine | 0.2 g |
| L-Threonine | 1.9 g |
| L-Alanine | 1.9 g |
| L-Proline | 1.0 g |
| L-Serine | 1.9 g |
| Glycine | 2.2 g |
| L-Aspartic acid | 1.1 g |
| L-Glutamic acid | 2.0 g |
| L-Arginine | 2.4 g |
| L-Histidine | 1.8 g |
| L-Lysine | 3.0 g |
| L-Tryptophan | 0.4 g |
| L-Cystine | 1.5 g |
| Soybean oil | 20.0 g |
| Yolk lecithin | 2.4 g |
| Oleic acid | 5.0 g |
| (b) Glucose | 120 g |
| Potassium acetate | 2.0 g |
| Calcium gluconate | 1.8 g |
| Magnesium sulfate | 0.7 g |
| Potassium dihydrogenphosphate | 1.1 g |
| Sodium chloride | 2.8 g |
| Potassium chloride | 0.3 g |
| Zinc sulfate | 5.8 mg |
| Thiamine hydrochloride | 8 mg |

EXAMPLE 5

(1) The ingredients (a) in such amounts as described in Table 10 except for L-cysteine were dissolved in distilled water for injection (400 ml) with heating at 90° C., and after cooling the resulting solution, L-cysteine was dissolved therein. The obtained solution was adjusted to pH 7.0 with malic acid and further a suitable amount of distilled water for injection was added to make the total amount of 500 ml. Thus an amino acid-infusion was prepared. The amino acid-infusion was filtered through Millipore filter having a pore size of 0.22 μm and filled into the first compartment of a bag having two compartments for infusion, and then the first compartment was hermetically sealed. The bag was made of a soft plastic (crosslinked ethylene-vinyl acetate copolymer).

(2) The ingredients (b) in such amounts as described in Table 10 except for thiamine hydrochloride were dissolved in distilled water for injection (400 ml) with warming at 60° C. and after cooling the resulting solution, thiamine hydrochloride was dissolved therein. The obtained solution was adjusted to pH 3.5 with malic acid and further a suitable amount of distilled water for injection was added thereto to make the total amount of 500 ml. Thus a saccharide-infusion was prepared. The saccharide-infusion was filtered through Millipore filter having a pore size of 0.22 μm, and filled into the second compartment of the bag wherein the above-mentioned amino acid-infusion was filled into the first compartment, and then the second compartment was hermetically sealed.

(3) The bag containing both infusions was heat-sterilized at 100° C. for 15 minutes, and then the bag and an oxygen absorber (AGELESS, Mitsubishi Gas Chemical Company, Inc., Japan) were put in an oxygen-impermeable bag made of a film of poly(vinyl alcohol) resin. The bag was hermetically sealed and then the TPN solution of the present invention was obtained.

TABLE 10

| Ingredient | Amount |
| --- | --- |
| (a) L-Isoleucine | 3.4 g |
| L-Leucine | 5.4 g |
| L-Valine | 3.6 g |
| L-Methionine | 1.56 g |
| L-Phenylalanine | 3.08 g |
| L-Tyrosine | 0.2 g |
| L-Threonine | 1.92 g |
| L-Alanine | 3.44 g |
| L-Proline | 2.56 g |
| L-Serine | 1.68 g |
| Glycine | 2.2 g |
| L-Aspartic acid | 0.2 g |
| L-Glutamic acid | 0.2 g |
| L-Arginine | 4.44 g |
| L-Histidine | 1.88 g |
| Lysine malate | 3.45 g |
| L-Tryptophan | 6.4 g |
| L-Cysteine | 6.2 g |
| (b) Glucose | 170 g |
| Potassium acetate | 1.5 g |
| Calcium gluconate | 1.2 g |
| Magnesium chloride | 0.5 g |
| Potassium dihydrogenphosphate | 1.0 g |
| Sodium L-lactate | 2.5 g |
| Sodium chloride | 1.0 g |
| Potassium chloride | 0.5 g |
| Thiamine hydrochloride | 5 mg |

EXAMPLE 6

(1) The ingredients (a) in such amounts as described in Table 11 were dissolved in distilled water for injection (400 ml) with heating at 90° C. After cooling the resulting solution, the resulting solution was adjusted to pH 7.0 with succinic acid and further a suitable amount of distilled water for injection was added thereto to make the total amount of 500 ml. Thus an amino acid-infusion was prepared. The amino acid-infusion was filtered through Millipore filter having a pore size of 0.22 μm and filled into the first compartment of a bag having two compartments for infusion, and then the first compartment was hermetically sealed. The bag was made of a soft plastic (crosslinked ethylene-vinyl acetate copolymer).

(2) The ingredients (b) in such amounts as described in Table 11 except for thiamine hydrochloride were dissolved in distilled water for injection (400 ml) with warming at 60° C. and after cooling the resulting solution, thiamine hydrochloride was dissolved therein. The obtained solution was adjusted to pH 3.5 with succinic acid and further a suitable amount of distilled water for injection was added thereto to make the total amount of 500 ml. Thus a saccharide-infusion was prepared. The saccharide-infusion was filtered through Millipore filter having a pore size of 0.22 μm, and filled into the second compartment of the bag wherein the above-mentioned amino acid-infusion was filled into the first compartment, and then the second compartment was hermetically sealed.

(3) The bag containing both infusions was heat-sterilized at 105° C. for 10 minutes, and then the bag and an oxygen absorber (AGELESS, Mitsubishi Gas Chemical Company, Inc., Japan) were put in an oxygen-imparmeable bag made of a film of poly(vinyl alcohol) resin. The bag was hermetically sealed and then the TPN solution of the present invention was obtained.

TABLE 11

| Ingredient | Amount |
| --- | --- |
| a) L-Isoleucine | 1.2 g |
| L-Leucine | 2.2 g |
| L-Valine | 1.4 g |
| L-Methionine | 0.8 g |
| L-Phenylalanine | 2.0 g |
| L-Tyrosine | 0.12 g |
| L-Threonine | 1.0 g |
| L-Alanine | 1.6 g |
| L-Proline | 2.0 g |
| L-Serine | 0.9 g |
| Glycine | 3.1 g |
| L-Aspartic acid | 0.4 g |
| L-Glutamic acid | 0.2 g |
| L-Arginine | 2.1 g |
| L-Histidine | 1.0 g |
| Lysine malate | 2.8 g |
| L-Tryptophan | 0.37 g |
| L-Cystine | 0.05 g |
| (b) Glucose | 150 g |
| Potassium acetate | 1.2 g |
| Calcium gluconate | 2.0 g |
| Magnesium chloride | 1.0 g |
| Potassium dihydrogenphosphate | 1.0 g |
| Sodium L-lactate | 3.5 g |
| Sodium chloride | 1.2 g |
| Potassium chloride | 0.8 g |
| Zinc sulfate | 5 mg |
| Thiamine hydrochloride | 5 mg |

EXAMPLE 7

(1) The ingredients (a) in such amounts as described in Table 12 except for L-cysteine were dissolved in distilled water for injection (800 ml) with heating at 90° C., and after cooling the resulting solution, L-cysteine was dissolved therein. The obtained solution was adjusted to pH 7.0 with succinic acid and further a suitable amount of distilled water for injection was added thereto to make the total amount of 1000 ml. Thus an amino acid-infusion was prepared. The amino acid-infusion was filtered through Millipore filter having a pore size of 0.22 μm and filled into the first compartment of a bag having two compartments for infusion, and then the first compartment was hermetically sealed. The bag was made of a soft plastic (crosslinked ethylene-vinyl acetate copolymer).

(2) The ingredients (b) in such amounts as described in Table 12 except for thiamine hydrochloride were dissolved in distilled water for injection (800 ml) with warming at 60° C. and after cooling the resulting solution, thiamine hydrochloride was dissolved therein. The obtained solution was adjusted to pH 3.5 with succinic acid and further a suitable amount of distilled water for injection was added thereto to make the total amount of 1000 ml. Thus a saccharide-infusion was prepared. The saccharide-infusion was filtered through Millipore filter having a pore size of 0.22 μm, and filled into the second compartment of the bag wherein the above-mentioned amino acid-infusion was filled into the first compartment, and then the second compartment was hermetically sealed.

(3) The bag containing both infusions was heat-sterilized at 105° C. for 10 minutes, and then the bag and an oxygen absorber (AGELESS, Mitsubishi Gas Chemical Company, Inc., Japan) were put in an oxygen-imparmeable bag made of a film of poly(vinyl alcohol) resin. The bag was hermetically sealed and then the TPN solution of the present invention was obtained.

TABLE 12

| Ingredient | Amount |
| --- | --- |
| (a) L-Isoleucine | 3.4 g |
| L-Leucine | 7.5 g |
| L-Valine | 2.7 g |
| L-Methionine | 2.5 g |
| L-Phenylalanine | 6.0 g |
| L-Tyrosine | 0.3 g |
| L-Threonine | 3.5 g |
| L-Alanine | 4.0 g |
| L-Proline | 2.0 g |
| L-Serine | 1.0 g |
| Glycine | 6.5 g |
| L-Aspartic acid | 2.5 g |
| L-Glutamic acid | 4.5 g |
| L-Arginine | 4.6 g |
| L-Histidine | 5.2 g |
| Lysine malate | 8.0 g |
| L-Tryptophan | 1.0 g |
| L-Cysteine | 0.6 g |
| Calcium gluconate | 3.6 g |
| (b) Glucose | 300 g |
| Potassium acetate | 4.0 g |
| Magnesium chloride | 1.5 g |
| Potassium dihydrogenphosphate | 2.5 g |
| Sodium chloride | 5.0 g |
| Zinc sulfate | 10 mg |
| Thiamine hydrochloride | 5 mg |

In addition to the ingredients used in the Examples, other ingredients can be used in the Examples as set forth in the specification to obtain substantially the same results.

What is claimed is:

1. A total parenteral nutrition solution to be prepared before using which comprises two separate infusions of an amino acid-infusion and a glucose-infusion wherein both of said infusions contain no sulfite ion, either one of said infusions contains vitamin $B_1$, a pH of the infusion containing vitamin $B_1$, is 2 to 4, a pH of the other infusion is 5 to 8, and a pH of the total parenteral nutrition solution prepared by mixing both infusions is 4 to 8.

2. The solution of claim 1 wherein the infusion containing vitamin $B_1$ is the glucose-infusion.

3. The solution of claim 1 wherein either one or both of the amino acid-infusion and the glucose-infusion contains an electrolyte.

4. The solution of claim 1 wherein one infusion contains a phosphate ion source and the other infusion contains a calcium ion source.

* * * * *